United States Patent
Wang et al.

(10) Patent No.: US 8,546,604 B2
(45) Date of Patent: Oct. 1, 2013

(54) POLYVINYL CHLORIDE RESIN PLASTICISER

(75) Inventors: Hao Wang, Seoul (KR); Seung Gweon Hong, Daejeon (KR); Tae Wook Kwon, Daejeon (KR); Jae Suk Koh, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 83 days.

(21) Appl. No.: 13/063,092

(22) PCT Filed: Sep. 4, 2009

(86) PCT No.: PCT/KR2009/005021
§ 371 (c)(1), (2), (4) Date: Mar. 9, 2011

(87) PCT Pub. No.: WO2010/030095
PCT Pub. Date: Mar. 18, 2010

(65) Prior Publication Data
US 2011/0166270 A1    Jul. 7, 2011

(30) Foreign Application Priority Data

Sep. 11, 2008  (KR) .................. 10-2008-0089868

(51) Int. Cl.
*C07C 69/34* (2006.01)

(52) U.S. Cl.
USPC ............... 560/146; 560/8; 560/76; 524/285; 524/306; 252/182.28

(58) Field of Classification Search
USPC ............... 524/285, 306; 560/127, 8, 76, 146
See application file for complete search history.

(56) References Cited

U.S. PATENT DOCUMENTS

| | | | | |
|---|---|---|---|---|
| 2,711,999 | A | * | 6/1955 | Brandner et al. ............ 524/290 |
| 5,104,569 | A | | 4/1992 | Leenhouts et al. |
| 6,740,773 | B2 | * | 5/2004 | Bohnen et al. .............. 560/127 |
| 7,208,545 | B1 | * | 4/2007 | Brunner et al. ............. 524/569 |
| 2005/0042393 | A1 | | 2/2005 | Lee et al. |
| 2008/0188601 | A1 | * | 8/2008 | Grass et al. ................ 524/321 |
| 2011/0206907 | A1 | * | 8/2011 | Hurley et al. ............. 428/195.1 |

FOREIGN PATENT DOCUMENTS

| | | | |
|---|---|---|---|
| JP | 71016587 B | * | 4/1966 |
| JP | 10-204438 | | 8/1998 |
| JP | 2002363366 A | * | 12/2002 |
| JP | 2006306773 A | * | 11/2006 |

OTHER PUBLICATIONS

STIC EICsearch May 16, 2012; see "13063092-392754-EICsearch.pdf".*

* cited by examiner

*Primary Examiner* — Peter F Godenschwager
*Assistant Examiner* — Jane L Stanley
(74) *Attorney, Agent, or Firm* — Abelman, Frayne & Schwab

(57) ABSTRACT

The invention relates to a diol-ester based plasticizer prepared by reacting a diol and a carboxylic acid for use with a polyvinyl chloride resin composition to impart improved physical properties, such as hardness and tensile strength.

11 Claims, No Drawings

POLYVINYL CHLORIDE RESIN PLASTICISER

CROSS-REFERENCE TO RELATED APPLICATIONS

This application is a National Phase of PCT/KR2009/005021, filed 4 Sep. 2009, which claims priority from KR No. 10-2008-0089868, filed 11 Sep. 2008, both of which are incorporated herein by reference.

TECHNICAL FIELD

The present invention relates to an ester compound and a plastic comprising the same, and, particularly, to a plasticizer for a polyvinyl chloride (PVC) resin. More precisely, the present invention relates to an ester plasticizer prepared using the esterification reaction of diol and carboxylic acid, by which a polyvinyl chloride resin composition having high plasticizing efficiency and improved physical properties such as hardness, tensile strength and the like can be manufactured.

BACKGROUND ART

A polyvinyl chloride resin, which is a homopolymer or a copolymer including 50% or more of polyvinyl chloride, is a commonly-used resin which can be formed into various products by extrusion molding, injection molding, calendering or the like. Such a polyvinyl chloride resin is widely used as a raw material for various products, such as pipes, electric wires, electric appliances, toys, films, sheets, synthetic leathers, tarpaulins, tape, packing materials for foods, medical supplies and the like. Various physical properties can be provided to such a polyvinyl chloride resin by suitably adding various additives such as a plasticizer, a stabilizer, filler, pigment and the like.

Among such additives, a plasticizer is an essential additive providing various physical properties and functions, such as workability, flexibility, electrical insulation, adhesivity and the like, to a polyvinyl chloride resin. Low volatility, as a very important factor of a plasticizer, is important both when a plasticizer is mixed in a plastic composition and when a shaped product containing a plasticizer is practically used. Further, plasticizers used in the field of foods, drinks, medical supplies and medicines must be harmless to the human body for health. A typical example of such harmless plasticizers is a phthalate plasticizer. However, it is predicted that the usage of a phthalate plasticizer will be remarkably reduced in the future because of the criticism regarding its toxicity attributable to its reactivation under the laws regulating toxic materials. Therefore, it is required to develop a plasticizer that includes an ester whose basic structure does not contain phthalate and which has a plasticizing efficiency equal to that of a phthalate plasticizer.

DISCLOSURE

Technical Problem

In order to solve the above-mentioned problem, the present inventors carefully examined ester compounds that could be used as a plasticizer for a polyvinyl chloride resin. As a result, they found that a specifically-structured novel ester compound can be used as a plasticizer, and, particularly, is excellent as a plasticizer for a polyvinyl chloride resin. Based on these findings, the present invention was completed. Accordingly, an object of the present invention is to provide a novel ester plasticizer prepared using diol and having physical properties equal to or superior to conventional phthalate plasticizers.

Another object of the present invention is to provide a plasticizer composition comprising the novel ester plasticizer.

Still another object of the present invention is to provide a polyvinyl chloride resin composition comprising the plasticizer composition.

Technical Solution

In order to accomplish the above objects, a first aspect of the present invention provides an ester plasticizer, represented by Formula 1 below:

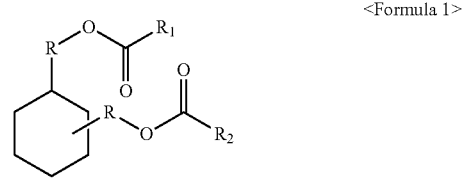

<Formula 1> wherein R is $(CH_2)_n$, n is an integer of 0 to 2, $R_1$ is a substituted or unsubstituted alkyl group of 4 to 16 carbon atoms, and $R_2$ is a substituted or unsubstituted naphthenic group or aryl group of 5 to 10 carbon atoms.

A second aspect of the present invention provides an ester plasticizer composition, comprising the ester plasticizer in an amount of 50~100 wt %.

A third aspect of the present invention provides a polyvinyl chloride resin composition, comprising the ester plasticizer composition in an amount of 10~100 phr based on a polyvinyl chloride resin.

Advantageous Effects

When a polyvinyl chloride resin is manufactured using the ester plasticizer using diol according to the present invention, there are advantages in that a product having excellent plasticizing efficiency can be obtained, and in that the physical properties such as tensile strength and the like of the product are improved.

BEST MODE

Hereinafter, an ester plasticizer and a polyvinyl chloride resin composition comprising the ester plasticizer according to the present invention will be described in detail.

The ester plasticizer of the present invention, prepared by reacting diol, particularly, cyclohexanediol with at least one kind of carboxylic acid, is represented by Formula 1 below:

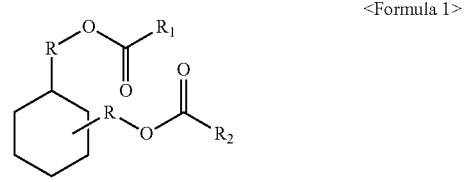

<Formula 1> wherein R is $(CH_2)_n$, n is an integer of 0 to 2, $R_1$ is a substituted or unsubstituted alkyl group of 4 to 16 carbon atoms, and $R_2$ is a substituted or unsubstituted naphthenic group or aryl group of 5 to 10 carbon atoms.

More preferably, $R_1$ may be a substituted or unsubstituted alkyl group of 6 to 10 carbon atoms, and $R_2$ may be a substituted or unsubstituted naphthenic group or aryl group of 5 to 8 carbon atoms.

$R_1$ and $R_2$ each independently may include a straight-chain or branched-chain alkyl group of 4 to 20 carbon atoms, an alkenyl group of 4 to 20 carbon atoms, a cycloalkyl group of 4 to 20 carbon atoms or an aryl group of 6 to 10 carbon atoms as a substituent group.

The ester plasticizer is prepared by the esterification reaction of 1,4-cyclohexane dimethanol with aromatic carboxylic acid and fatty acid. The molar ratio of aromatic carboxylic acid and fatty acid to 1,4-cyclohexane dimethanol is 1:1.8~0.4:1.8~0.4, preferably 1:1.0~0.5:0.7~1.6. This molar ratio thereof is determined based on the hydroxy group existing in 1,4-cyclohexane dimethanol. It is preferred that an acid catalyst, for example, sodium bisulfate be used in the esterification reaction. Further, p-toluenesulfonic acid, sulfuric acid or the like can be used as the catalyst in the esterification reaction. The catalyst may be used in an amount of 0.5~5 wt % based on a reaction mixture.

Meanwhile, examples of the solvents usable in the esterification reaction include hexane, cyclohexane, toluene and xylene. It is preferred that the esterification reaction be conducted at 100~160☐. After the esterification reaction, unreacted organic acid and acid catalyst are neutralized by the addition of an alkali reagent such as an aqueous sodium carbonate solution or an aqueous calcium carbonate solution. The coarse ester obtained after phase separation is washed with water, dewatered and then filtered to obtain an object.

The plasticizer composition of the present invention includes the ester plasticizer represented by Formula 1 above in an amount of 50~100 wt %. This plasticizer composition may further include a compound represented by Formula 2 below and/or a compound represented by Formula 3 below in an amount of less than 50 wt % based on the total amount of the ester plasticizer composition:

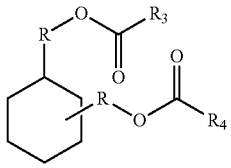

[Formula 2]

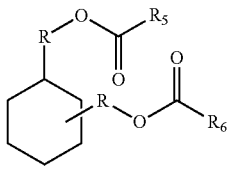

[Formula 3]

wherein R is $(CH_2)_n$, n is an integer of 0 to 2, $R_3$ and $R_4$ are each independently a substituted or unsubstituted alkyl group of 4 to 16 carbon atoms, and $R_5$ and $R_6$ are each independently a substituted or unsubstituted cycloparaffin or aryl group of 6 to 10 carbon atoms.

Further, $R_3$ to $R_6$ each independently may include a straight-chain or branched-chain alkyl group of 4 to 20 carbon atoms, an alkenyl group of 4 to 20 carbon atoms, a cycloalkyl group of 4 to 20 carbon atoms or an aryl group of 6 to 10 carbon atoms as a substituent group.

The ester plasticizer of the present invention is suitably used in a polyvinyl chloride resin. The polyvinyl chloride resin is not limited to polyvinyl chloride. Examples of the polyvinyl chloride resin may include: chlorine-containing resins, such as chlorinated polyvinyl chloride, polyvinylidene chloride, chlorinated polyethylene, polyvinyl chloride acetate copolymer, polyvinyl chloride ethylene copolymer, polyvinyl chloride propylene copolymer, polyvinyl chloride styrene copolymer, polyvinyl chloride isobutylene copolymer, polyvinyl chloride vinylidene copolymer, polyvinyl chloride ether copolymers, and blends thereof, and blends, block copolymers and graft copolymers of the chlorine-containing resins and resins containing no chlorine such as acylonitrile-styrene copolymer, acrylonitrile-styrene-butadiene terpolymer, ethylene-vinyl acetate copolymer, polyesters, etc.

The polyvinyl chloride resin composition of the present invention includes the ester plasticizer composition in an amount of 10~100 phr based on a polyvinyl chloride resin. The amount of the ester plasticizer composition may be suitably adjusted according to the use of polyvinyl chloride resin composition. When the amount of the ester plasticizer composition is less than 10 phr, flexibility or workability, which can be exhibited by a plasticizer, cannot be realized. Further, when the amount thereof is greater than 100 phr, it is difficult to ensure necessary mechanical properties, and it is probable that the polyvinyl chloride resin composition will elute.

Meanwhile, the polyvinyl chloride resin composition may further include additives, excluding filler and pigment, in an amount of 0~30 phr based on the polyvinyl chloride resin.

Here, examples of the additives, which are general additives that can be selectively included in the polyvinyl chloride resin composition, may include an insulation improver, various kinds of metal salts, polyols, epoxy compounds, a phenolic or sulfuric antioxidant, an ultraviolet absorber, a hindered amine-based photostabilizer, an inorganic stabilizer, an anti-fogging agent, an anti-misting agent, an auxiliary stabilizer, organic tin compounds, and the like.

Unlike the general additives, filler and pigment can be included up to about 200 phr based on the polyvinyl chloride resin. When the amount of the filler and pigment is greater than 200 phr, the density, hardness or flexibility of the polyvinyl chloride resin composition is negatively influenced. Examples of the filler may include calcium carbonate, silica, clay, glass beads, mica, sericite, glass flakes, asbestos, wolastonite, potassium titanate, polarization-maintaining fiber (PMF), gypsum fiber, xonotlite, metal-oxide semiconductor (MOS), phosphate fiber, glass fiber, carbon fiber, aramid fiber, and the like.

The polyvinyl chloride resin composition including the ester plasticizer of the present invention can be used in building materials, such as wall-finishing materials, floor materials, window sashes, wallpaper, and the like; wire covering materials; interior and exterior materials for automobiles; agricultural materials, such as materials for vinyl houses, tunnels and the like; food wrappers; film-forming agents, such as sealant, plastisol, paint, ink and the like; and miscellaneous goods, such as synthetic leather, coated fabrics, hoses, pipes, sheets, toys for infants, gloves and the like. However, the present invention is not limited thereto.

Methods of preparing the polyvinyl chloride resin composition using the ester plasticizer composition are not particularly limited, and are well known in the related field.

MODE FOR INVENTION

Hereinafter, the present invention will be described in more detail with reference to the following Examples. However, these Examples are set forth to illustrate the present invention, and the scope of the present invention is not limited thereto. In these Examples, the physical properties of samples were evaluated by the following method.

Hardness

Based on the ASTM D2240, the needle of a hardness tester (A type) was completely pressed onto one point of a sample for 5 seconds, and then the hardness of the sample was measured. Hardness tests were conducted at three points of each sample, and then the average value thereof was obtained. Hardness is used as an index for representing plasticizing efficiency.

Tensile Strength, Elongation, Elastic Modulus at 100% Elongation

The tensile strength and elastic modulus of a sample were measured using UTM based on the ASTM D412 method. The tensile strength and elastic modulus thereof were measured at the cut point of a dumbbell-shaped sample after it was pulled at a crosshead speed of 200 mm/min. The elastic modulus at 100% elongation corresponds to the tensile strength at 100% elongation, and is closely related to plasticizing efficiency.

Maximum Torque

The maximum torque occurring at the time of mixing a polyvinyl chloride with a plasticizer was measured using a Brabender tester.

Example 1

Preparation of an Ester Plasticizer Using 1,4-Cyclohexane Dimethanol, Benzoic Acid and 2-Ethylhexanoic Acid First, 1.0 mol of 1,4-cyclohexane dimethanol, 0.6 mol of benzoic acid, 1.2 mol of 2-ethylhexanoic acid, 200 g of toluene as a solvent, and 3.0 g of sodium bisulfate as a catalyst were put into a 2 L round flask provided with a stirrer and a condenser, and were then heated to 100° C. to conduct a reaction for 12 hours.

After the reaction, unreacted organic acid were depressurized to 5 mmHg at 200□ by a vacuum pump, neutralized by 10 wt % of an aqueous sodium carbonate solution, water-washed, dewatered and then filtered by an adsorbent to obtain a plasticizer composition. It was found that the plasticizer composition includes 4-(2-ethyl-hexanoyloxymethyl)-cyclohexylmethyl ester (about 50 wt %) represented by Formula 1 above as major component.

Preparation of a Polyvinyl Chloride Resin Composition

Test samples were fabricated in order to evaluate the performance of the obtained ester plasticizer. That is, 50 phr of the obtained plasticizer composition including the compound represented by Formula 1 above as major component and 1 phr of a stabilizer (LFX-1100) were mixed with a polyvinyl chloride resin (LS-100, manufactured by LG Chemicals Co., Ltd.) of part by weight, and then the mixture was preheated to 185° C. for 1 minute, pressurized for 1.5 minutes and cooled for 2 minutes to obtain a sheet having a thickness of 2 mm. The sheet was formed into various dumbbell-shaped test samples.

The above-mentioned tests were conducted using these test samples, and the results thereof are given in Table 1 below.

Example 2

An ester plasticizer and a polyvinyl chloride resin composition were prepared in the same manner as Example 1, except that decanoic acid was used instead of 2-ethylhexanoic acid. The test results thereof are given in Table 1 below.

Example 3

An ester plasticizer and a polyvinyl chloride resin composition were prepared in the same manner as Example 1, except that naphthenic acid was used instead of benzoic acid. The test results thereof are given in Table 1 below.

Comparative Example 1

A test sample was fabricated in the same manner as Example 1 using di-2-ethylhexyl phthalate as a plasticizer. The same test that had been conducted in Example 1 was conducted using this test sample, and the results thereof are given in Table 1 below.

Comparative Example 2

A test sample was fabricated in the same manner as Example 1 using diisononyl phthalate as a plasticizer instead of di-2-ethylhexyl phthalate. The same test that had been conducted in Example 1 was conducted using this test sample, and the results thereof are given in Table 1 below.

Comparative Example 3

A test sample was fabricated in the same manner as Example 1 using trioctyl trimellitate as a plasticizer. The same test that had been conducted in Example 1 was conducted using this test sample, and the results thereof are given in Table 1 below.

TABLE 1

| Measured items | Ex. 1 | Ex. 2 | Ex. 3 | Co. Ex. 1 | Co. Ex. 2 | Co. Ex. 3 |
|---|---|---|---|---|---|---|
| Hardness (Shore A) | 80 | 78 | 81 | 81 | 84 | 87 |
| Tensile strength (Kgf/cm2) | 217 | 213 | 210 | 189 | 193 | 226 |
| Elongation (%) | 352 | 365 | 368 | 370 | 373 | 373 |
| Modulus (Kgf/cm2) | 93 | 83 | 84 | 85 | 96 | 117 |
| Maximum torque (Nm) | 4.4 | 4.5 | 4.2 | 4.6 | 4.5 | 4.4 |

From the results of Table 1 above, it can be presumed that the plasticizing efficiency of the plasticizers of Examples 1, 2, and 3 is higher than that of the plasticizers of Comparative Examples 1, 2 and 3, and that the physical properties, such as tensile strength, elongation and the like, of the plasticizers of Examples 1, 2, and 3 are equal to or greater than those of the plasticizers of Comparative Examples 1, 2 and 3. Therefore, it is expected that, since the novel plasticizer of the present invention has high plasticizing efficiency, it can be formed in various shapes, and thus it can be variously utilized.

As described above, although the preferred embodiments of the present invention have been disclosed for illustrative purposes, those skilled in the art will appreciate that various modifications, additions and substitutions are possible, without departing from the scope and spirit of the invention as disclosed in the accompanying claims. Therefore, the present invention is not limited to the above Examples.

The invention claimed is:

1. An ester plasticizer, represented by Formula 1 below:

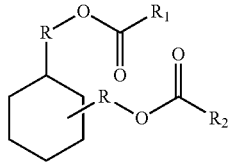

<Formula 1> wherein R is $(CH_2)_n$, is an integer of 0 to 2, $R_1$ is a substituted or unsubstituted alkyl group of 4 to 16 carbon atoms, and $R_2$ is a substituted or unsubstituted naphthenic group or aryl group of 5 to 10 carbon atoms.

2. The ester plasticizer according to claim 1, wherein $R_1$ is a substituted or unsubstituted alkyl group of 6 to 10 carbon atoms, and $R_2$ is a substituted or unsubstituted naphthenic group or aryl group of 5 to 8 carbon atoms.

3. The ester plasticizer according to claim 1, wherein $R_1$ and $R_2$ each independently are substituted by a straight-chain or branched-chain alkyl group of 4 to 20 carbon atoms, an alkenyl group of 4 to 20 carbon atoms, a cycloalkyl group of 4 to 20 carbon atoms or an aryl group of 6 to 10 carbon atoms.

4. An ester plasticizer composition, comprising the ester plasticizer of claim 1 in an amount of 50~100 wt %.

5. The ester plasticizer composition according to claim 4, further comprising at least one of compounds represented by Formulae 2 and 3 below in an amount of less than 50 wt % based on the total amount of the ester plasticizer composition:

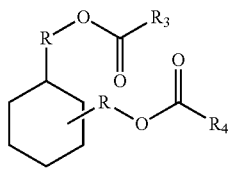

<Formula 2>

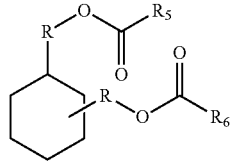

<Formula 3> wherein R is $(CH_2)_n$, n is an integer of 0 to 2, $R_3$ and $R_4$ are each independently a substituted or unsubstituted alkyl group of 4 to 16 carbon atoms, and $R_5$ and $R_6$ are each independently a substituted or unsubstituted cycloparaffin or aryl group of 6 to 10 carbon atoms.

6. The ester plasticizer composition according to claim 5, wherein $R_3$ to $R_6$ each independently are substituted by a straight-chain or branched-chain alkyl group of 4 to 20 carbon atoms, an alkenyl group of 4 to 20 carbon atoms, a cycloalkyl group of 4 to 20 carbon atoms or an aryl group of 6 to 10 carbon atoms.

7. A polyvinyl chloride resin composition, comprising the ester plasticizer composition of claim 4 in an amount of 10~100 phr based on a polyvinyl chloride resin.

8. A polyvinyl chloride resin composition comprising the ester plasticizer composition of claim 5 in an amount of 10~100 phr based on a polyvinyl chloride resin.

9. A polyvinyl chloride resin composition comprising the ester plasticizer composition of claim 6 in an amount of 10~100 phr based on a polyvinyl.

10. The polyvinyl chloride resin composition according to claim 7, further comprising additives, excluding filler and pigment, up to 30 phr based on a polyvinyl chloride resin.

11. The ester plasticizer according to claim 2, wherein $R_1$ and $R_2$ each independently are substituted by a straight-chain or branched-chain alkyl group of 4 to 20 carbon atoms, an alkenyl group of 4 to 20 carbon atoms, a cycloalkyl group of 4 to 20 carbon atoms or an aryl group of 6 to 10 carbon atoms.

* * * * *